United States Patent

Inoue et al.

[11] Patent Number: 5,863,907
[45] Date of Patent: Jan. 26, 1999

[54] CARBOXYMETHYLMANNOGLUCANS AND DERIVATIVES THEREOF

[75] Inventors: Kazuhiro Inoue, Funabashi; Teruomi Ito, Matsudo; Takayuki Kawaguchi, Toshima-Ku; Katsutoshi Aono, Nara; Satoshi Okuno, Misato; Toshiro Yano, Kashiwa, all of Japan

[73] Assignee: Drug Delivery System Institute, Ltd., Japan

[21] Appl. No.: 681,981

[22] Filed: Jul. 30, 1996

Related U.S. Application Data

[62] Division of Ser. No. 397,560, Mar. 2, 1995, Pat. No. 5,567,690, which is a continuation of Ser. No. 136,039, filed as PCT/JP92/00784 Feb. 21, 1992, abandoned, which is a division of Ser. No. 934,501, Oct. 21, 1992, abandoned.

[30] Foreign Application Priority Data

Feb. 21, 1991 [JP] Japan ........................... 3-27544
Dec. 27, 1991 [JP] Japan ........................... 3-360395

[51] Int. Cl.[6] .................... A61K 31/725; A61K 31/715; A61K 31/72; A61K 47/36
[52] U.S. Cl. ................... 514/54; 514/61; 514/777; 536/123; 536/123.1; 536/123.12
[58] Field of Search ............... 514/54, 61, 777; 536/123, 123.1, 123.12

[56] References Cited

U.S. PATENT DOCUMENTS

| | | |
|---|---|---|
| 4,202,966 | 5/1980 | Misaki et al. . |
| 4,237,266 | 12/1980 | Sugiura et al. . |
| 4,396,611 | 8/1983 | Duc . |
| 4,454,289 | 6/1984 | Nakajima et al. . |
| 4,454,315 | 6/1984 | Sasaki et al. ........................... 536/18.2 |
| 4,603,197 | 7/1986 | Kadoya et al. . |
| 4,872,885 | 10/1989 | Tsubakimoto et al. . |
| 5,026,735 | 6/1991 | Stern . |
| 5,124,363 | 6/1992 | Stern . |
| 5,204,457 | 4/1993 | Maruno et al. . |
| 5,567,690 | 10/1996 | Inoue et al. ........................... 514/54 |

FOREIGN PATENT DOCUMENTS

| | | |
|---|---|---|
| 0 323 627 | 7/1989 | European Pat. Off. . |
| 384416A1 | 8/1990 | European Pat. Off. . |
| 45-395217 | 12/1970 | Japan . |
| 54-14513 | 2/1979 | Japan . |
| 5414513 | 2/1979 | Japan . |
| 61-152634 | 7/1986 | Japan . |
| 63-31082 | 12/1988 | Japan . |
| 1-190636 | 7/1989 | Japan . |

OTHER PUBLICATIONS

Inoue et al., *Carbohydrate Research*, 123, 305–314 (1983).
Inoue et al., *Carbohydrate Research*, 114, 245–256 (1983).
Inoue et al, Carb. Res. 123:305–314 (1983).
Ueda et al, Chem. Pharm. Bull. 37(6):1639–1641 (1989).

*Primary Examiner*—Francisco Prats
*Attorney, Agent, or Firm*—Wenderoth, Lind & Ponack, L.L.P.

[57] ABSTRACT

A carboxymethylmannoglucan comprising tetrasaccharide units represented by the following general formula (I) and salt thereof. Further, the invention discloses a carboxymethylmannoglucan derivative and salt thereof produced by subjecting part or the whole of mannose of the tetrasaccharide units to ring opening and subjecting part or the whole of glucose which constitute the main chain but have no mannose as a branch

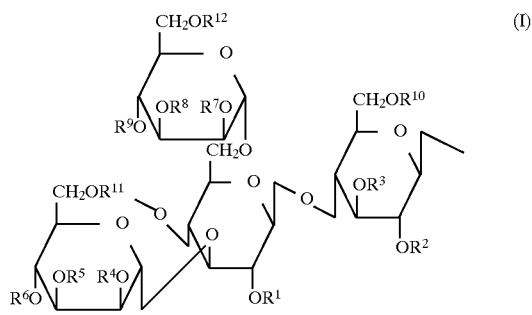

wherein $R^1$ to $R^{12}$ each represent a hydrogen atom or a carboxymethyl group.

The compounds are useful as carrier for delaying the disappearance of a drug in the blood and for enhancing the organotropism of the drug for a carcinoma.

6 Claims, 7 Drawing Sheets

CARBOXYMETHYLMANNOGLUCANS AND DERIVATIVES THEREOF

This is a divisional application of Ser. No. 08/397,560, filed Mar. 2, 1995, now U.S. Pat. No. 5,567,690, which is a continuation of abandoned Ser. No. 08/136,039, filed Oct. 14, 1993, which is a divisional of abandoned Ser. No. 07/934,501, filed Oct. 21, 1992, which is a 371 of PCT/JP92/00184, filed Feb. 21, 1992.

BACKGROUND OF THE INVENTION

1. Technical Field

The present invention relates to novel carboxymethylmannoglucans and derivatives and salts thereof. More particularly, the present invention is concerned with a carboxymethylmannoglucan and derivatives and salts thereof for use as a carrier useful for delaying the disappearance of a drug in the blood and for enhancing the organotropism of the drug for a carcinoma.

2. Background Art

An attempt to use a water-soluble polymer as a carrier for a drug has hitherto been made especially in the field of a pharmaceutical preparation, and many related techniques for this purpose have been proposed in the art. In many of these proposals, use is made of cellulose derivatives such as carboxymethyl cellulose, hydroxypropyl cellulose and hydroxypropyl methylcellulose, and the dispersion and sustained release of the drug are intended by virtue of physical and chemical properties of these substances per se. While in these attempts the drug is mixed homogeneously with the cellulose derivatives as a carrier, the drug is not chemically bonded to the carrier.

In the so-called "technique for organotropism" wherein a drug is delivered by a necessary amount at a desired time to a target organ, when a water-soluble polymer is utilized as a carrier for a drug, the drug and the carrier should be chemically bonded to each other rather than mere mixing. Examples of such attempts include bonding of mitomycin C to dextran (Hitoshi Sezaki, Yakugaku Zasshi, 109, 611–621 (1989)), bonding of mitomycin C to mannan (Report in the 49th General Meeting of The Japanese Cancer Association, (1990), page 425, theme No. 2155), bonding of bleomycin to mannan (Report in the 49th General Meeting of The Japanese Cancer Association, (1990), page 425, theme No. 2154), etc. The present status, however, is that no sufficient development is made on the technique wherein a polysaccharide type water-soluble polymer is newly synthesized and a drug is chemically bonded to this polymer to deliver the drug.

SUMMARY OF THE INVENTION

Under the above circumstances, the present inventors have aimed at a polysaccharide polymer comprising a mannoglucan and attempted to carboxymethylate the mannoglucan and, as a result, have found that the resultant substance is a novel polysaccharide-type, water-soluble polymer which is useful as a carrier for use in a technique wherein a drug is delivered by chemically bonding a drug to the carrier, particularly a technique for delaying the disappearance in the blood of the drug and for enhancing the migration of the drug to a carcinoma.

Specifically, an object of the present invention is to provide a polysaccharide-type, water-soluble polymer having a drug through a chemical bond and capable of properly delivering a drug.

Another object of the present invention is to provide a polysaccharide-type, water-soluble polymer useful for delaying the disappearance of a drug in the blood and enhancing the organotropism of the drug for a carcinoma.

According to a first aspect of the present invention, there is provided a carboxymethylmannoglucan comprising tetrasaccharide units represented by the general formula (I) or salt thereof.

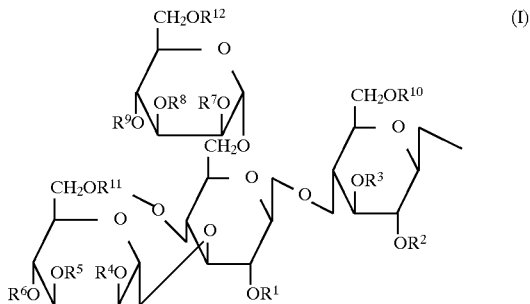

wherein $R^1$, $R^2$, $R^3$, $R^4$, $R^5$, $R^6$, $R^7$, $R^8$, $R^9$, $R^{10}$, $R^{11}$ and $R^{12}$ which may be the same or different each represent a hydrogen atom or $CH_2COOH$.

The second aspect of the present invention provides a carboxymethylmannoglucan derivative comprising tetrasaccharide units represented by the general formula (III) or salt thereof:

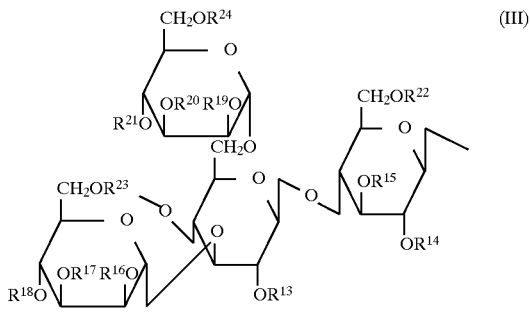

wherein $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ which may be the same or different each represent a hydrogen atom, $CH_2COOH$, $CH_2CONR^{*1}R^{*2}$ wherein $NR^{*1}R^{*2}$ represents a residue formed by removing one hydrogen atom from an amino group of a drug which has an amino group and is represented by the general formula $HNR^{*1}R^{*2}$, $CH_2COOR^{*3}$ wherein $OR^{*3}$ represents a residue formed by removing a hydrogen atom from an alcoholic hydroxyl group of a drug which has an alcoholic hydroxyl group and is represented by the general formula $HOR^3$, or $[CH_2COO\cdot 1/2[Pt(NH_3)_2]]$ wherein Pt represents a divalent platinum, with the proviso that at least one of $R^{13}$ to $R^{24}$ in the molecule represents $CH_2CONR^{*1}R^{*2}$, $CH_2COOR^{*3}$ or $[CH_2COO\cdot 1/2[Pt(NH_3)_2]]$.

Further, the third aspect of the present invention provides a oxidized carboxymethylmannoglucan or derivative thereof comprising units represented by the general formula (IV) and/or units represented by the following general formula (V) or salt thereof:

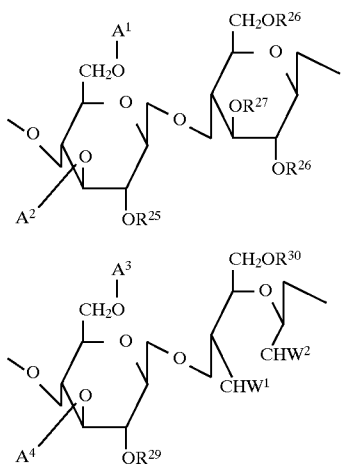

(IV)

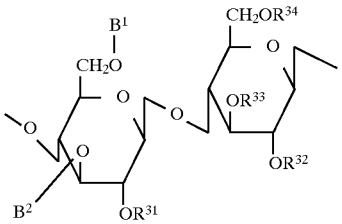

(V)

wherein $R^{25}$, $R^{26}$, $R^{27}$, $R^{28}$, $R^{29}$ and $R^{30}$ which may be the same or different each represents a hydrogen atom or $CH_2COOH$;

$W^1$ and $W^2$ each represent $=O$ or $=N-R^{*4}$ wherein R represents a residue formed by removing two hydrogen atoms from an amino group of a drug which has an amino group and is represented by the general formula $H_2N-R^{*4}$.

$A^1$ and $A^2$ which may be the same or different each represent a group represented by the formula (VI), (VII), (VIII) or (IX);

$A^3$ and $A^4$ which may be the same or different each represent a group represented by the following formula (VII), (VIII) or (IX), with the proviso that when the molecule consists of units represented by the general formula (IV) alone, not all the $A^1$ and $A^2$ in the molecule do not represent the formula (VI);

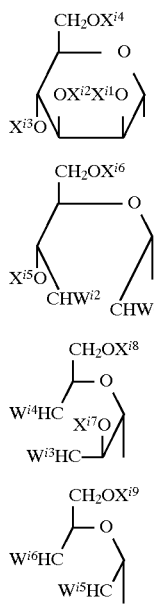

(VI)

(VII)

(VIII)

(IX)

wherein $X^{i1}$, $X^{i2}$, $X^{i3}$, $X^{i4}$, $X^{i5}$, $X^{i6}$, $X^{i7}$, $X^{i8}$ and $X^{i9}$ which may be the same or different each represent a hydrogen atom or $CH_2COOH$; and $W^{i1}$, $W^{i2}$, $W^{i3}$, $W^{i4}$, $W^{i5}$ and $W^{i6}$ which may be the same or different each represent $=O$ or $=N-R^{*4}$ wherein $=N-R^{*4}$ represent a residue formed by removing two hydrogen atoms from an amino group of a drug which has an amino group and is represented by the general formula $H_2N-R^{*4}$, with the proviso that each suffix "i" of $X^{i1}$ to $X^{i9}$ and $W^{i1}$ to $W^{i6}$ in the formulae (VI), (VII), (VIII) and (IX) represents an integer of 1 to 4, and $A^1$, $A^2$, $A^3$ and $A^4$ are generally herein referred to as "$A^i$".

The fourth aspect of the present invention provides a carboxymethyl ring-opening-mannoglucan and derivative thereof comprising units represented by the general formula (X) and/or units represented by the following general formula (XI) or salt thereof:

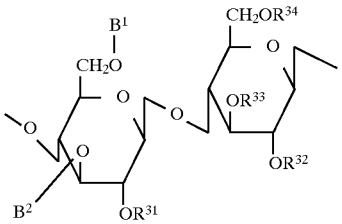

(X)

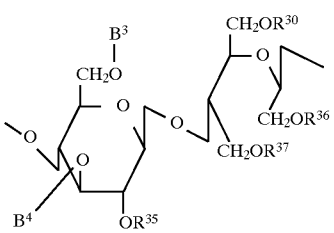

(XI)

wherein $R^{30}$, $R^{31}$, $R^{32}$, $R^{33}$, $R^{34}$, $R^{35}$, $R^{36}$ and $R^{37}$ which may be the same or different represents a hydrogen atom, $CH_2COOH$, $CH_2CONR^{*1}R^{*2}$, $CH_2COOR^{*3}$ wherein $NR^{*1}R^{*2}$ and $OR^{*3}$ each have the same meaning as that defined in formula (III), or $CH_2COO\text{-}1/2[Pt(NH_3)_2]$ wherein Pt represents a divalent platinum;

$B^1$ and $B^2$ which may be the same or different each represent a group represented by the formula (XII), (XIII), (XIV) or (IX);

$B^3$ and $B^4$ which may be the same or different each represent a group represented by the formula (XIII), (XIV) or (XV), with the proviso that when the molecule consists of units represented by the general formula (X) alone, not all the $B^1$ and $B^2$ represent a group represented by the formula (XII);

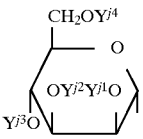

(XII)

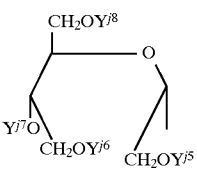

(XIII)

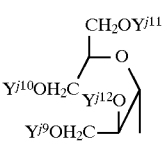

(XIV)

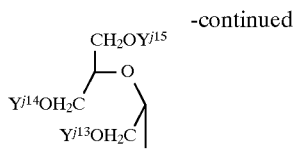

-continued (XV)

wherein $Y^{j1}, Y^{j2}, Y^{j3}, Y^{j4}, Y^{j5}, Y^{j6}, Y^{j7}, Y^{j8}, Y^{j9}, Y^{j10}, Y^{j11}, Y^{j12}, Y^{j13}, Y^{j14}$ and $Y^{j15}$ which may be the same or different each represent a hydrogen atom, $CH_2COOH$, $CH_2CONR^{*1}R^{*2}$ or $CH_2COOR^{*3}$ wherein $NR^{*1}R^{*2}$ and $OR^{*3}$ each have the same meaning as that defined in formula (III), or $CH_2COO \cdot 1/2[Pt(NH_3)_2]$ wherein Pt represents a divalent platinum;

with the proviso that each suffix "j" of $Y^{j1}$ to $Y^{j15}$ in the formulae (XII), (XIII), (XIV) and (XV) represent an integer of 1 to 4, and $B^1, B^2, B^3$ and $B^4$ are generally herein referred to as "$B^j$".

DETAILED DESCRIPTION OF THE INVENTION

Compound

Figure 1:
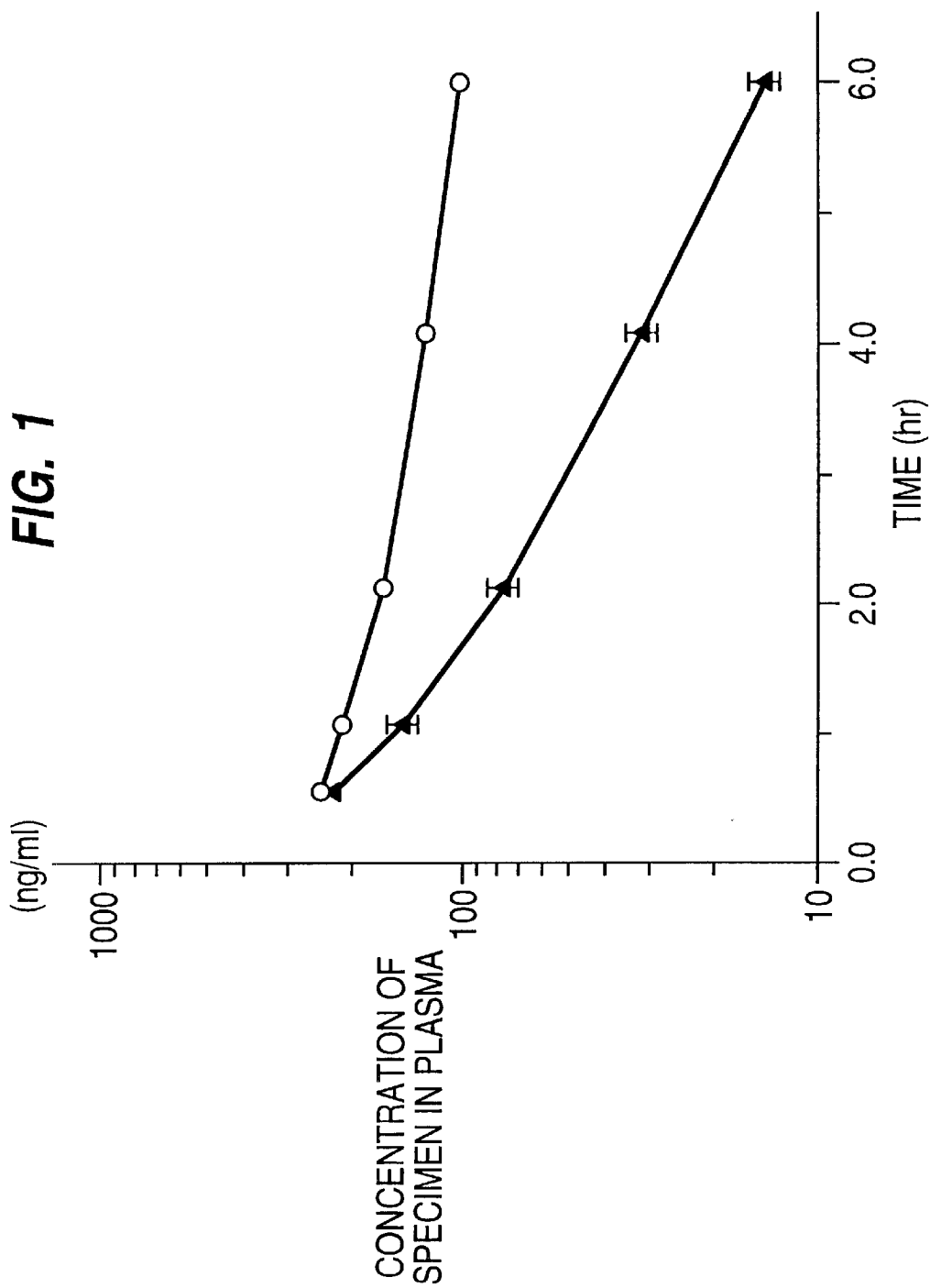
FIG. 1 is a graph showing a change in the concentration of a specimen in plasma when the specimen has been administered to rats bearing Walker 256 at a dose of 18.0 μg/kg.

The carboxymethylmannoglucan according to the first aspect of the present invention comprises tetrasaccharide units represented by the general formula (I). The term "comprises tetrasaccharide units" used herein is intended to mean that the carboxymethylmannoglucan according to the present invention is a polymer compound having a structure comprising said units as repeating units.

The tetrasaccharide units represented by the general formula (I) has a basic skeleton represented by the following formula (II). Hence, the carboxymethylmannoglucan according to the present invention has a basic skeleton of a polysaccharide comprising tetrasaccharide units represented by the following formula (II).

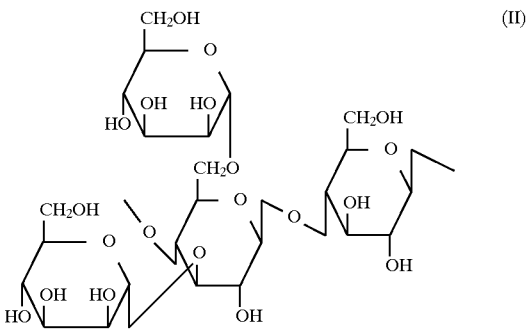

This polysaccharide polymer has been already reported by one of the present inventors (Inoue K. et al., Carbohydrate Res., 114, 245–256, (1983)).

The polysaccharide having this basic skeleton is a D-manno-D-glucan, and the main chain of the polysaccharide is a glucan having a β (1→4) bond. The polysaccharide has such a structure that an D-mannosyl group is bonded to every other D-glucose residue at its 3-position and 6-position through an α (1→3) bond and an α (1→6) bond to form double branching.

The structure can be represented by the following formula besides the formula (II).

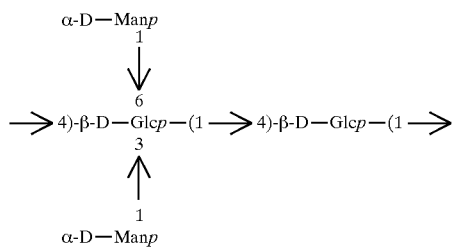

The molecular weight of the carboxymethylmannoglucan according to the present invention is not limited so far as the carboxymethylmannoglucan comprises tetrasaccharide units represented by the general formula (I). The molecular weight is preferably in the range from $1 \times 10^4$ to $2 \times 10^6$, still preferably about $1 \times 10^6$.

The carboxymethylmannoglucan according to the present invention, in other words, has such a structure that the hydrogen atom of the hydroxyl group in the above basic skeleton is substituted with a carboxymethyl group. The proportion of introduction of the substituent can be expressed by the degree of substitution defined in terms of the number of substituents per saccharide residue. Specifically, it can be expressed by the following equation:

Degree of substitution =

$$\frac{\text{total number of substituents in molecule}}{(\text{total number of tetrasaccharide units in molecule} \times 4)}$$

The upper limit of the degree of substitution is 3 in which all the hydroxyl groups are substituted. In the present invention, the degree of substitution is preferably 0.01 or more. In the present invention, at least one carboxymethyl group should be present in the molecule. In this sense, the compound having a degree of substitution of 0 is excluded. It is needless to say that positions of introduction of the substituent in adjacent tetrasaccharide units may be the same or different so far as the structure of individual tetrasaccharide units can be represented by the general formula (I).

The carboxymethylmannoglucan according to the present invention can exist in the form of a salt. Suitable examples of the salt include alkali metal or alkaline earth metal salts, such as sodium salt, potassium salt and calcium salt, and amino acid salts such as arginine salt and lysine-salt.

The carboxymethylmannoglucan derivative according to the second aspect of the present invention is derived from a carboxymethylmannoglucan represented by the general formula (I). Specifically, the mannoglucan derivative comprising units represented by the general formula (III) has such a structure that in the general formula (I) a drug is carried on part or the whole of the carboxymethyl group through an acid amide bond, an ester bond or a covalent bond.

Examples of the introducible drug include the following compounds. Specifically, drug which has an amino group and is represented by the general formula $HNR^{*1}R^{*2}$ are introducible through an acid amide bond, and specific examples thereof include daunorubicin, doxorubicin, mitomycin C and bleomycin. Drugs which have an alcoholic hydroxyl group and are represented by the general formula $HOR^{*3}$ are introducible through an ester bond, and specific examples thereof include cyclocytidine, vincristine, vinblastine and adrenalin. Further, platinum complexes such as cisplatin are introducible through a covalent bond.

Although the molecular weight of the carboxymethylmannoglucan derivative according to the second aspect of the present invention is not limited, it is preferably in the range from $1\times10^4$ to $2\times10^6$, still preferably about $1\times10^5$. In any case, the proportion of introduction of the substituent, i.e., the degree of substitution is less than 3, and the lower limit exceeds zero (0). The degree of substitution is preferably about 1 to 2.

The carboxymethylmannoglucan derivative according to the second aspect of the present invention as well can exist in the form of a salt of the carboxymethyl group. Examples of the favorable salt include alkali metal or alkaline earth metal salts, such as sodium salt, potassium salt and calcium salt, and amino acid salts such as arginine salt and lysine salt.

The oxidized carboxymethylmannoglucan and its derivative according to the third aspect of the present invention comprise units represented by the general formula (IV) and units represented by the general formula (V). The term "derivative" used herein is used only for a compound wherein a drug has been introduced through a chemical bond. Therefore, the carboxymethylmannoglucan according to the third aspect of the present invention has a structure having an aldehyde group at its cleaved end formed by cleaving part or the whole of mannosyl groups of tetrasaccharide units constituting the carboxymethylmannoglucan represented by the general formula (I) and further cleaving part or the whole of glucose residues which constitute the main chain but have no mannose as a branch. Further, it can be said that the oxidized carboxymethylmannoglucan derivative according to the third aspect of the present invention is such that a drug has been further introduced into the aldehyde group through a Schiff's base-type bond.

In the general formula (IV), $A^1$ and $A^2$ each represent a group represented by the formula (VI), (VII), (VIII) or (IX). In this connection, the case where the molecule consists of units represented by the general formula (IV) alone and all the $A^1$ and $A^2$ are a group represented by the formula (VI) is excluded. The group represented by the formula (VII), (VIII) or (IX) is one formed by cleaving the bond between the 2-position and the 3-position of the mannose residue represented by the formula (VI), one formed by cleaving the bond between the 3-position and the 4-position or one formed by cleaving the bond between the 2-position and the 3-position and the bond between the 3-position and the 4-position.

In the general formula (V), $A^3$ and $A^4$ each represent a group represented by the formula (VI), (VII), (VIII) or (IX).

In the formulae (VI), (VII), (VIII) and (IX), each suffix "i" of $X^{i1}$ to $X^{i9}$ and $W^{i1}$ to $W^{i6}$ in the formulae (VI), (VII), (VIII) and (IX) represents an integer of 1 to 4, and $A^1$, $A^2$, $A^3$ and $A^4$ are generally herein referred to as "$A^i$". This means that, for example, a case where each of $A^1$ and $A^2$ branched from the same D-glucose is a group represented by the formula (VII) and a case where two $X^{i5}$, i.e., $X^{15}$ and $X^{25}$, are independent of and different from each other fall within the scope of the present invention. Further, in units adjacent to each other represented by the general formula (IV) and/or general formula (V) in the molecule, $R^{25}$ to $R^{30}$ and Al to $A^4$ and $X^{i1}$ to $X^{i9}$ and $W^{i1}$ to $W^{i6}$ may be different from each other.

Although the ratio of existence of a unit represented by the general formula (IV) to a unit represented by the general formula (V), and the ratio of existence of groups represented by the formulae (VI), (VII), (VIII) and (IX) are not particularly limited, they may be determined by taking the kind and the hydrophilicity of the drug to be introduced into consideration.

Drugs which have an amino group and are represented by the general formula $H_2N-R^{*4}$ are introducible through a Schiff's base-type bond, and specific examples thereof include daunorubicin, doxorubicin and bleomycin.

The carboxymethyl ring-opening-mannoglucan and derivative thereof according to the fourth aspect of the present invention comprises units represented by the general formula (X) and/or units represented by the general formula (XI). The carboxymethyl ring-opening-mannoglucan according to the fourth aspect of the present invention has a structure formed by opening the ring of part or the whole of mannosyl groups of tetrasaccharide units constituting the mannoglucan and opening the ring of part or the whole of glucose residues which constitute the main chain but have no mannose as a branch. Hereafter substituting with a carboxymethyl group part or the whole of the hydrogen atom of the hydroxymethyl group which is formed by the opening of the ring described above. Further, the carboxymethyl ring-opening-mannoglucan derivative according to the fourth aspect of the present invention has such a structure that a drug is carried on the carboxymethyl group through an acid amide bond, an ester bond or a covalent bond.

In the general formula (X), $B^1$ and $B^2$ each represent a group represented by the formula (XII), (XIII), (XIV) or (XV). In this connection, the compound which consists of units represented by the general formula (X) where $B^1$ and $B^2$ are a group represented by the formula (XII) is excluded from the present invention because the compound is D-manno-D-glucan perse. The groups represented by the formula (XIII), (XIV) or (XV) are one formed by cleaving the bond between the 2-position and the 3-position of the mannose residue represented by the formula (XII), one formed by cleaving the bond between the 3-position and the 4-position or one formed by cleaving the bond between the 2-position and the 3-position and the bond between the 3-position and the 4-position.

In the general formula (X), $B^3$ and $B^4$ each represent a group represented by the formula (XIII), (XIV) or (XV). In this connection, a case where $B^3$ and $B^4$ each represent a group represented by the formula (XII) is excluded. This is because when the ring opening of the mannoglucan by oxidation is conducted, the mannose as a branched saccharide preferentially undergoes cleaving through oxidation over D-glucose which constitute the main chain but has no mannose as a branch.

In the formulae (XII), (XIII), (XIV) and (XV), suffix "j" of $Y^{j1}$ to $Y^{j15}$ represents an integer of 1 to 4, and $B^1$, $B^2$, $B^3$ and $B^4$ are generally herein referred to as "$B^j$". This means that, for example, a case where each of $B^1$ and $B^2$ branched from the same D-glucose is a group represented by the formula (XIII) and a case where two $Y^{j5}$, i.e., $Y^{15}$ and $Y^{25}$, are independent of and different from each other as well fall within the scope of the present invention. Further, in units adjacent to each other represented by the general formula (X) and/or general formula (XI) in the molecule, $R^{31}$ to $R^{38}$ and $B^1$ to $B^4$ and $Y^{j1}$ to $Y^{j15}$ may be different from each other.

Although the ratio of existence of a unit represented by the general formula (X) to a unit represented by the general formula (XI), and the ratio of existence of groups represented by the formulae (XII), (XIII), (XIV) and (XV) are not particularly limited, they may be determined by taking the kind and the hydrophilicity of the drug to be introduced into consideration.

The carboxymethyl ring-opening-mannoglucan according to the fourth aspect of the present invention is favorable because it has a higher water solubility than the carboxymethylmannoglucan according to the first aspect of the present invention while having the carboxymethyl group into which a drug can be introduced.

Examples of the drug which can be introduced into the carboxymethyl group of the part or the whole of the carboxymethyl ring-opening-mannoglucan according to the fourth aspect of the present invention through an acid amide bond, an ester bond or a covalent bond include drugs introducible into the mannoglucan derivative according to the second aspect of the present invention.

Although the molecular weight of the carboxymethylmannoglucan and its derivative according to the third aspect of the present invention and the carboxymethyl ring-opening-mannoglucan and derivative thereof according to the fourth aspect of the present invention is not limited, it is preferably in the range from $1 \times 10^4$ to $2 \times 10^6$.

The proportion of introduction of the carboxymethyl group, i.e., the degree of substitution is less than 3, and the lower limit exceeds zero (0). In the case of the oxidized carboxymethylmannoglucan and its derivative, the degree of substitution is preferably 0.4 to 1.

The carboxymethylmannoglucan and its derivative and the carboxymethyl ring-opening-mannoglucan and derivative thereof as well can exist in the form of a salt of the carboxymethyl group. Favorable examples of the salt include those as described with respect to the carboxymethylmannoglucans according to the first and second aspects of the present invention.

Preparation of Compound and its Applications

The carboxymethylmannoglucan according to the first aspect of the present invention can be prepared by substituting a hydrogen atom of a hydroxyl group of a mannoglucan comprising tetrasaccharide units represented by the formula (II) with a carboxymethyl group. Specifically, it may preferably be prepared by reacting a mannoglucan comprising tetrasaccharide units represented by the formula (II) with a halogenoacetic acid or its salt in the presence of an alkali. For example, it can be prepared by dissolving a starting compound in water, adding sodium hydroxide to the solution, adding monochloroacetic acid thereto while cooling, stirring the mixture at room temperature for about 20 hr, adjusting the pH value to about 8 to 9, pouring the reaction mixture into methanol, collecting the resultant precipitate, washing the precipitate with methanol and acetone and drying the washed precipitate. In this case, the degree of substitution of the carboxymethyl group can be regulated through a variation in the amount of addition of the alkali and monochloroacetic acid or its salt.

The mannoglucan comprising tetrasaccharide units represented by the formula (II) may preferably be prepared from a purification product separated from a filtrate of a culture of a microorganism belonging to Actinomycete, for example, *Microellobosporia grisea* (Japanese Patent Publication No. 52402/1989).

The carboxymethylmannoglucan according to the first aspect of the present invention has a small rate of disappearance in the blood and an organotropism prosperity for a carcinoma (for details, see the following Experiment Examples). Since the carboxymethylmannoglucan according to the present invention has many hydroxyl groups and carboxyl groups, a drug can be bonded through these functional groups. Therefore, the carboxymethylmannoglucan according to the first aspect of the present invention can be used as a carrier useful in a technique wherein a drug is carried through a chemical bond for delivering the drug, particularly a technique wherein the rate of disappearance of drug in the blood is lowered to enhance the migration of the drug to a carcinoma.

The introduction of the drug into the carboxymethylmannoglucan according to the present invention can be conducted through a selection of a suitable method depending upon the properties of the drug. For example, in the case of a drug having an amino group (for example, daunorubicin or doxorubicin), the introduction can be conducted by oxidizing the carboxymethylmannoglucan according to the present invention with periodic acid or the like to form an aldehyde group and bonding thereto a drug as a Schiff's base. Similarly, in the case of a drug having an amino group, it is also possible to bond the drug to the carboxyl group through an amide bond. Furthermore, after the hydroxyl group is activated with cyanogen bromide, a drug having an amino group is bonded thereto through an isourea bond. In the above methods, the drug having an amino group may be one having in itself an amino group or one having an amino group newly provided for the purpose of conducting bonding. Further, it is also possible to use a method which comprises selecting a suitable spacer having an amino group and adding the spacer to form a compound corresponding to a drug having an amino group.

Specific examples of the compound wherein a drug has been introduced into the carboxymethylmannoglucan of the first aspect of the present invention include the carboxymethylmannoglucan derivative of the second aspect of the present invention. The derivative to which a drug has been introduced through an acid amide bond or an ester bond may preferably be prepared by reacting a carboxymethylmannoglucan comprising units represented by the general formula (I) or its salt with a drug represented by the general formula $HNR^{*1}R^{*2}$ or the general formula $HOR^{*3}$ under an acid amide bond or ester bond forming condition. For example, a derivative having daunorubicin introduced thereinto may preferably be prepared by reacting carboxymethylmannoglucan with daunorubicin hydrochloride in, for example, a borate buffer (pH: 8) in the presence of 1-ethyl-3-(3-dimethylaminopropyl)carbodiimide hydrochloride (EDC) as a condensing agent and precipitating the product from ethanol. A derivative having a drug introduced through a covalent bond may preferably be prepared, for example, by reacting cis-dinitrate-diamine-platinum (II) as a platinum complex with carboxymethylmannoglucan in an aqueous solution, conducting dialysis and precipitating the product from ethanol.

The oxidized carboxymethylmannoglucan according to the third aspect of the present invention may preferably be prepared by subjecting carboxymethylmannoglucan comprising units represented by the general formula (I) to oxidation for ring opening. At first, an oxidizing agent (e.g., periodic acid or its salt) is added to the carboxymethylmannoglucan with ice cooling, and a reaction is allowed to moderately proceed at room temperature or below. The oxidized carboxymethylmannoglucan can be obtained, for example, by dialyzing the reaction mixture against water, adding sodium acetate as a precipitation agent, dropwise adding the mixture in ethanol to give a product as a precipitate. It is also possible to convert the mannosyl group-and the glucose residue to an aldehyde group to various degree through a variation in the amount of addition of periodic acid or its salt, thereby forming a carrier to which a desired amount of a drug can be bonded. Further, the degree of conversion to an aldehyde may be regulated through a variation in the reaction time, reaction temperature and other parameters. With respect to the conversion to an aldehyde, reference may be made to Inoue K. et al., Carbohydrate Res., 123, 305–314 (1983).

A drug represented by the general formula $H_2NR^{*4}$ can be reacted with the carboxymethylmannoglucan thus prepared under a Schiff base-type bond forming condition to give a derivative having a drug carrier thereon. For example, a derivative having daunorubicin introduced as a drug may preferably be prepared by reacting the oxidized carboxymethylmannoglucan with daunorubicin hydrochloride in a borate buffer (pH: 8)/ethanol mixed solution.

The carboxymethyl ring-opening-mannoglucan according to the fourth aspect of the present invention may preferably be prepared by opening the ring of mannoglucan through oxidation, reducing an aldehyde group formed by oxidation to form a hydroxymethyl group and introducing a carboxymethyl group into part or the whole of the hydroxymethyl group. For example, an oxidizing agent (e.g., sodium periodate) is added to an aqueous solution of mannoglucan, a reaction is moderately allowed to proceed at room temperature or below under a light shielding condition, and after the completion of the reaction, the reaction mixture is dialyzed against water. Then, sodium borohydride is added to the inner solution of dialysis, pH of the reaction mixture is adjusted to 5 and then 7, the reaction mixture is dialyzed against water, and the non-dialyzed solution is then concentrated to give a ring opened mannoglucan in a polyalcohol form. A carboxymethyl ring-opening-mannoglucan may preferably be prepared by dissolving the polyalcohol in an aqueous sodium hydroxide solution, adding monochloroacetic acid to the solution, allowing a reaction to proceed at room temperature, adjusting the pH of the reaction mixture to 8 and pouring the reaction mixture into ethanol.

To the carboxymethyl ring-opening-mannoglucan thus obtained, a drug may preferably be introduced as the same manner described with respect to the carboxymethylmannoglucan derivative according to the second aspect of the present invention.

EXAMPLES

Preparation

The mannoglucan as a starting compound in the following Examples was produced by *Microellobosporia grisea* (Institute for Fermentation, Osaka, deposit No.: IFO12518) as a production microorganism by the following method.

The above strain was inoculated by means of a slant into a Sakaguchi flask containing 100 ml of a GC medium (2% glucose, 0.5% peptone, 0.5% corn steep liquor, 0.3% yeast extract, 0.5% sodium chloride, 0.3% calcium carbonate, 1.5% agar; pH 7.0), and cultivated at 28° C. for 5 days while shaking. After 2 ml of the culture solution was inoculated into a Sakaguchi flask containing 100 ml of a GC medium, the cultivation was similarly conducted for 3 days. 200 ml of the culture solution was inoculated into a 30-liter jar fermentor containing 20 liters of a production medium (3% glucose, 2% corn steep liquor; pH 7.2), and stirred at 28° C. for 92 hr with aeration (10 liters/min, 250 rpm). Adekanol LG805 (manufactured by Asahi Denka Kogyo K. K.) was added as an antifoaming agent during the cultivation. The resultant medium was heated at 80° C. for 20 min, cooled to room temperature and filtered. The filtrate was passed through a column packed with Diaion PA306 (Cl⁻ type). And then 0.5 liter of 10% cetyl-pyridinium chloride and 1.0 liter of a 0.5M borate buffer (pH: 10) were added to the effluent and washings. The resultant precipitate was collected, washed with water and dissolved in 2% acetic acid (2.0 liters). After ethanol (6.0 liters) was added to the solution, the resultant precipitate was collected. The precipitate was washed with ethanol and dissolved in a 0.02% aqueous sodium acetate solution (3.0 liters). The precipitation was again conducted from the centrifugal supernatant with ethanol. The collected precipitate was washed with 75% ethanol, ethanol and acetone in that order and dried in vacuo over phosphorus pentaoxide at 50° C. for 8 hr to give 36 g of mannoglucan as an intended compound. The molecular weight (gel filtration method/standard substance: dextran, column: G5000PW) of the resultant mannoglucan was about $1 \times 10^6$.

Example 1

Water (20 ml) and sodium hydroxide (1.05 g) were added to the mannoglucan (500 mg) prepared in the Preparation 1 with stirring to give a clear solution. Monochloroacetic acid (1.5 g) was added and dissolved in the solution with cooling, and a reaction was allowed to proceed at room temperature for 20 hr with stirring. After the pH of the reaction mixture was adjusted to 8 with acetic acid, the mixture was poured into methanol (80 ml). The resultant white precipitate was then collected by filtration. The precipitate was washed with methanol and acetone in that order and dried in vacuo to give 481 mg of carboxymethylmannoglucan. This substance was designated as CM-1, and the degree of substitution (DS) per saccharide residue was measured according to the following method and found to be 0.08.

Measurement of Degree of Substitution

The degree of substitution (DS) was determined on a free acid form by the following back titration. Specifically, the carboxymethylmannoglucan prepared above was shaken together with 70% nritric acid/methanol (1:10 V/V) at room temperature for 3 hr, washed with 80% methanol and methanol using methyl red as an indicator, and dried to give a sample. This sample was dissolved in a predetermined excess of a 0.1 N aqueous sodium hydroxide solution and subjected to back titration with 0.1 N hydrochloric acid using phenolphthalein as an indicator. DS was determined by the following equation (I):

$$DS = 16.2\,(A-B)/[S - 5.8\,(A-B)]$$

wherein S (mg) is the amount of the sample, A (ml) is the predetermined excess of 0.1 N sodium hydroxide and B (ml) is the value of back titration of 0.1 N hydrochloric acid.

Examples 2 to 4

The procedure of Example 1 was repeated, except that the amounts of sodium hydroxide and monochloroacetic acid were varied as described in Table 1. The yield, degree of substitution and designated name of the substances prepared in Examples 1 to 4 are given in Table 1.

TABLE 1

| Ex. | NaOH (g) | MCA (g) | Yield (mg) | Degree of Substitution (DS) | Designated Name |
|-----|----------|---------|------------|-----------------------------|-----------------|
| 1   | 1.05     | 15      | 481        | 0.08                        | CM-1            |
| 2   | 1.75     | 2.5     | 503        | 0.17                        | CM-2            |
| 3   | 2.45     | 3.5     | 524        | 0.31                        | CM-3            |
| 4   | 3.50     | 5.0     | 598        | 0.53                        | CM-4            |

Note)
MCA: monochloroacetic acid

Example 5

20 ml of water and 3.5 g of sodium hydroxide were added to 500 mg of CM-4 (degree of substitution: 0.55) prepared in the same manner as Example 1 to give a clear solution. 5.0 g of monochloroacetic acid was added and dissolved in the solution with cooling, and a reaction was allowed to proceed at room temperature for 20 hr. After the pH of the reaction mixture was adjusted to 8 with acetic acid, the mixture was poured into 100 ml of methanol. The resultant precipitate was then collected by filtration. The precipitate was washed with methanol and dried in vacuo to give CM-5 (531 mg). The degree of substitution of CM-5 was 0.81.

Example 6

10 ml of water and 1.75 g of sodium hydroxide were added to CM-5 (250 mg) prepared in Example 5 to give a clear solution. 2.5 g of monochloroacetic acid was added and dissolved in the solution with cooling, and a reaction was allowed to proceed at room temperature for 21 hr. After the pH of the reaction mixture was adjusted to 8 with acetic acid, the mixture was poured into 60 ml of methanol. The resultant precipitate was then collected by filtration. The precipitate was washed with methanol and dried in vacuo to give CM-6 (261 mg). The degree of substitution of CM-6 was 1.0.

Experiment Example 1
(1) Sample and Specimen

CM-1 and CM-4 prepared in Examples 1 and 4 were used as a sample. The following experiment was conducted for preparing specimens for animal test from each sample. Specifically, each sample was dissolved in water, 0.5M sodium periodate was added in such an amount that the periodate ion corresponds to 0.1 mol per mol of the saccharide residue of the sample. A reaction was allowed to proceed at room temperature for 25 hr, and the reaction mixture was dialyzed against water at 4° C. Sodium acetate was added to the inner solution, and the mixture was poured into a 4-fold volume of ethanol. The resultant precipitate was washed with ethanol and acetone and dried. The powder thus obtained was reacted with sodium borohydride labelled with tritium in a 2.5 mM aqueous sodium carbonate solution at room temperature for 20 hr. After the pH of the reaction mixture was adjusted to 5 with acetic acid with cooling, the mixture was dialyzed against water. The inner solution was lyophilized to give specimen 1 and specimen 2.

(2) Method
i.) Maintenance of Tumor Cells

Walker 256 cells were intraperitoneally injected in an amount of $3\times10^6$ to $5\times10^6$ cells to Wistar/S rats (6 to 9 weeks of age, ♀), and succession was conducted every 7 days.

S-180 cells were intraperitoneally injected in an amount of $2\times10^6$ to $5\times10^6$ cells to ICR mice (4 to 6 weeks of age, ♂), and passage was conducted every 7 days.

ii.) Animals Bearing Tumors

Tumor cells were subcutaneously inoculated in an amount of $1.0\times10^7$ cells to the inguinal region of Wistar/S rats (6 weeks of age, ♀), and the rats were used as rats bearing Walker 256 6 days after the inoculation.

Tumor cells were subcutaneously implanted in an amount of $1.5\times10^6$ cells to the inquinal region of ICR mice (4 weeks of age, ♂), and the mice were used as mice bearing S-180 10 days after the implantation.

iii.) Distribution Study
Rats bearing Walker carcinosarcoma 256

Two experiments, i.e., one experiment under conditions of a dose of 18.0 μg/kg and 6 hr and another experiment under conditions of a dose of 10 mg/kg and 24 hr were conducted. A specimen was administered through the cervical vein of a rat bearing tumor under light ether anesthesia. Light ether anesthesia was conducted after a predetermined period of time, blood collection was conducted to determine the concentration of the specimen in plasma. The rats were subjected to bloodletting to determine the concentration of the specimen in the tumor and plasma 6 hr after the administration in the case of a dose of 18.0 μg/kg and 24 hr after the administration in the case of a dose of 10 mg/kg.

Mice bearing S-180

The specimen was administered at a dose of 18.0 μg/kg through a caudal vein of the mice bearing tumor. The mice were subjected to bloodletting to determine the concentration of the specimen in the tumor and plasma 4 hr after the administration.

The concentration of the specimen in the tumor and plasma were determined by burning the tumor and plasma in a combustion equipment and measuring the radioactivity by a liquid scintillation method.

(3) Results

Figure 2:
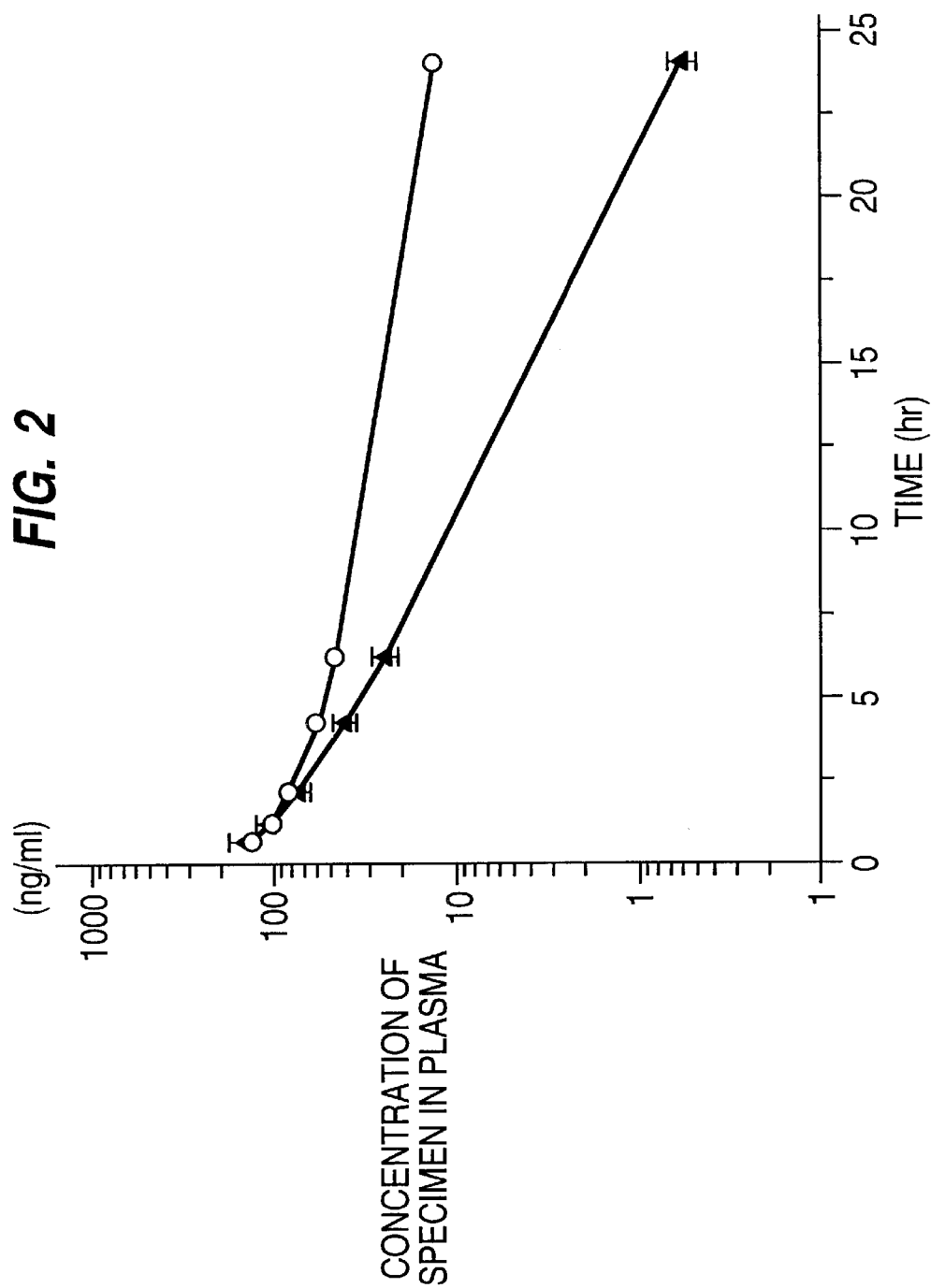
FIG. 2 is a graph showing a change in the concentration of a specimen in plasma when the specimen has been administered to rats bearing Walker 256 at a dose of 10 mg/kg.

The results are shown in FIG. 1, FIG. 2, Table 2 and Table 3. FIGS. 1 and 2 are respectively graphs showing a change in the concentration of a specimen in the plasma when the specimen was administered to the rat bearing Walker 256 at a dose of 18.0 μg/kg and at a dose of 10 mg/kg. In the Figures, a line of mark ▲ and a line of mark ○ respectively show the results of the specimen 1 and the specimen 2.

From the results shown in FIGS. 1 and 2, it is apparent that the substance according to the present invention does not rapidly disappear from the blood, and the diminution rate is low.

Tables 2 and 3 respectively show the concentration of the specimen in the tumor and plasma, and the Kp value of the tumor tissue defined below (which is simply referred to as "Kp" in the table) for the specimen 1 and the specimen 2. The Kp value is calculated according to the following equation.

$$Kp = \frac{\text{Concentration of specimen per g of tissue}}{\text{Concentration of specimen per ml of plasma}}$$

From Tables 2 and 3, it is apparent that the substance of the present invention has the organotropism for a carcinoma.

TABLE 2

|  | Concentration in Tumor (ng/g) | Concentration in Plasma (ng/ml) | Kp |
|---|---|---|---|
| Mice bearing S-180 (18.0 μg/kg, 4 hr) | 7.60 ± 0.49 | 2.36 ± 0.086 | 3.25 ± 0.30 |
| Rats bearing Walker 256 (18.0 μg/kg, 6 hr) | 24.4 ± 3.83 | 14.1 ± 1.72 | 1.73 ± 0.093 |
| Rats bearing Walker 256 (10 mg/kg, 24 hr) | 19,210 ± 630 | 575 ± 102 | 35.7 ± 6.31 |

TABLE 3

|  | Concentration in Tumor (ng/g) | Concentration in Plasma (ng/ml) | Kp |
|---|---|---|---|
| Mice bearing S-180 (18.0 μg/kg, 4 hr) | 5.10 ± 0.43 | 22.5 ± 1.16 | 0.226 ± 0.016 |
| Rats bearing Walker 256 (18.0 μg/kg, 6 hr) | 26.7 ± 2.35 | 97.5 ± 5.78 | 0.274 ± 0.017 |
| Rats bearing Walker 256 (10 mg/kg, 24 hr) | 11,050 ± 619 | 12,610 ± 1,110 | 0.891 ± 0.094 |

Experiment Example 2
(Synthesis of Carboxymethylmannoglucan-Daunorubicin Conjugate through Schiff Base-type Bond)

Figure 3:
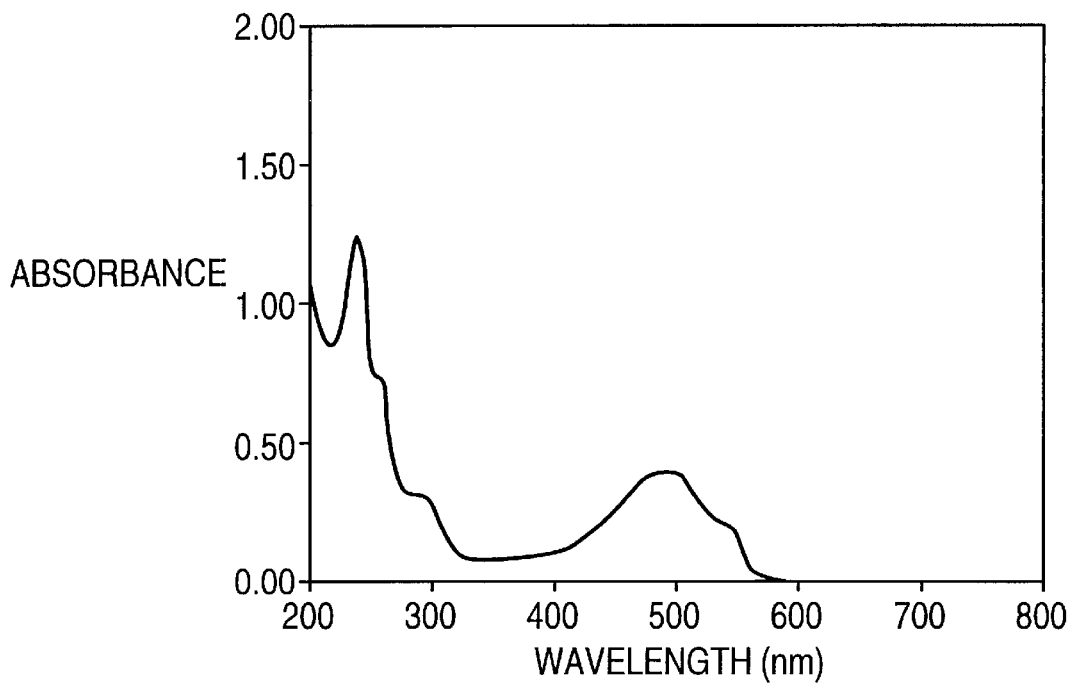
FIG. 3 is an ultraviolet-visible absorption spectrum of an oxidized carboxymethylmannoglucan-daunorubicin conjugate through a Schiff's base-type bond prepared in Experiment Example 2.

200 mg of CM-4 prepared in Example 4 was dissolved in 40 ml of water. A solution of 21 mg of sodium periodate (corresponding to 0.1 mol per mol of saccharide residue) dissolved in a small amount of water was added thereto with stirring under ice cooling. A reaction was allowed to proceed at room temperature for 25 hr, and the reaction mixture was dialyzed against water. 200 mg of sodium acetate was added to the inner solution and the mixture was dropwise added to 350 ml of ethanol. The resultant precipitate was collected, dried to give 192 mg of carboxymethylmannoglucan having aldehyde groupsr and 20 mg of the product was dissolved in 4 ml of a 0.1M borate buffer (pH: 8.0) A solution of 16.9 mg of daunorubicin hydrochloride dissolved in 4 ml of ethanol and 400 μl of a 0.1M borate buffer (pH: 8.0) was added thereto, and a reaction was allowed to proceed at room temperature overnight. 12 ml of ethanol was added to the reaction mixture, and the resultant precipitate was collected and dried to give 18 mg of carboxymethyl-mannoglucan-daunorubicin conjugate through a Schiff's base-type bond. This conjugate was soluble in water and had a daunorubicin content of 10.5% (% by weight). An ultraviolet-visible absorption spectrum (concentration: 200 μg/ml, solvent: water) of the conjugate is shown in FIG. 3.

Experiment Example 3
(Synthesis of Carboxymethylmannoglucan-Daunorubicin Conjugate through Amide Bond)

Figure 4:
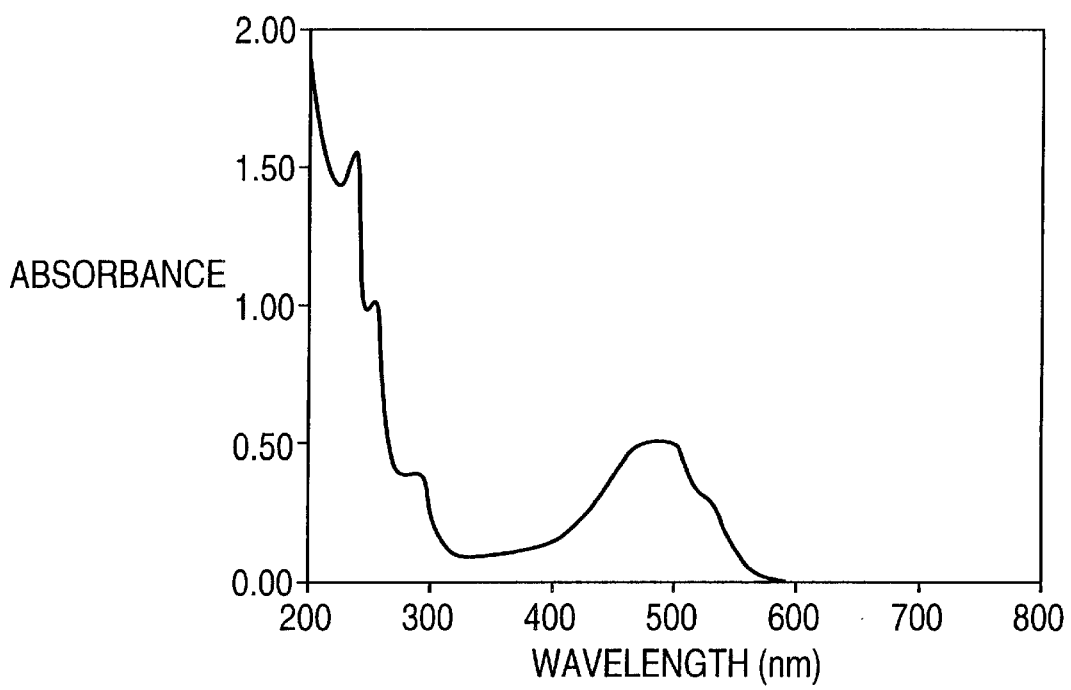
FIG. 4 is an ultraviolet-visible absorption spectrum of a carboxymethylmannoglucan-daunorubicin conjugate through an amide-bond prepared in Experiment Example 3.

20 mg of CM-4 prepared in Example 4 was dissolved in 6 ml of a 0.1M borate buffer (pH: 8.0). A solution of 5.6 mg of daunorubicin hydrochloride dissolved in 4 ml of ethanol and 1 ml of a 0.1M borate buffer (pH: 8.0) was added thereto, and a solution of 60 mg of 1-ethyl-3-(3-dimethylaminopropyl)carbodiimide hydrochloride dissolved in 1 ml of water was further added. A reaction was allowed to proceed at room temperature overnight. 24 ml of ethanol was added to the reaction mixture, and the resultant precipitate was collected and dried to give 20 mg of a carboxymethylmannoglucan-daunorubicin conjugate wherein the drug is bonded to the carboxyl group through an amide bond. This conjugate was soluble in water and had a daunorubicin content of 5.3% (% by weight). An ultraviolet-visible absorption spectrum (concentration: 500 μg/ml, solvent: water) of the conjugate is shown in FIG. 4.

Example 7

Mannoglucan (3.00 g) was carboxymethylated in the same manner as that of Example 4 to give 3.25 g of CM-4 (degree of substitution: 0.53). The CM-4 (2.00 g) was carboxymethylated again in the same method as that of Example 5 to give 2.22 g of CM-5 (degree of substitution: 0.79). The CM-5 (1.00 g) was further carboxymethylated in the same manner as that of Example 6 to give 1.08 g of CM-6 (degree of substitution: 1.0).

Example 8

CM-6 (500 mg) prepared in Example 7 was suspended in 2-propanol (30 ml), and the whole amount of a solution of 1 g of sodium hydroxide dissolved in 3 ml of water was dropwise added thereto. Thereafter, monochloroacetic acid (1 g) was added, and a reaction was allowed to proceed at room temperature for 2 hr with stirring. The precipitate in the reaction mixture was collected, and a reaction was again allowed to proceed at room temperature for 20 hr through the use of 2-propanol (40 ml)/sodium hydroxide (1 g)-water (2 ml)/monochloroacetic acid (1 g). The precipitate in the reaction mixture was collected, dissolved in water (40 ml) and poured into methanol (240 ml). The resultant precipitate was collected, washed with methanol and dried in vacuo to give 620 mg of CM-7 (degree of substitution: 2.1).

Example 9

Mannoglucan (4.00 g) was dissolved in 0.1 N hydrochloric acid (160 ml), the solution was subjected to acid degradation at 80° C. for 5 hr, and the reaction mixture was neutralized with 5 N sodium hydroxide. The solution was poured into ethanol (500 ml), and the resultant precipitate was collected. The precipitate was washed with ethanol and dissolved in water (250 ml). This solution was passed through both columns of Dowex 50W-X2 (H⁺) and Dowex 1-X2 (Cl⁻) (each 1.5×20 cm), and the solution passed through the columns was concentrated to about 150 ml. The concentrate was poured into ethanol (500 ml), and the resultant precipitate was collected and washed with ethanol and dried in vacuo to give 3.48 g of a low-molecular mannoglucan.

3.30 g of the low-molecular mannoglucan was dissolved in 1M sodium chloride (330 ml), methanol (330 ml) was added thereto, and the mixture was centrifuged. Methanol (110 ml) was added to the resultant supernatant, and the resultant precipitate was collected. The precipitate was dissolved in water (50 ml) and poured into ethanol (200 ml), and the resultant precipitate was collected, washed with ethanol and dried in vacuo to give 1.92 g of a low-molecular mannoglucan (MG15). The molecular weight of MG15 (gel filtration method/standard substance: dextran, column: G4000PW$_{XL}$) was about 1.5×10$^5$.

Example 10

Mannoglucan (7.00 g) was dissolved in 0.1 N hydrochloric acid (280 ml), the solution was subjected to acid degradation at 80° C. for 7.5 hr, and the reaction mixture was neutralized with 5 N sodium hydroxide. The solution was poured into ethanol (900 ml), and the resultant precipitate was collected. The precipitate was washed with ethanol and dissolved in water (450 ml). This solution was passed through both columns of Dowex 50W-X2 (H$^+$) and Dowex 1-X2 (Cl$^-$) (each 2×20 cm), and the solution passed through the columns was concentrated to about 250 ml. The concentrate was poured into ethanol (850 ml), and the resultant precipitate was collected and washed with ethanol and dried in vacuo to give 6.02 g of a low-molecular mannoglucan.

3.98 g of the low-molecular mannoglucan was dissolved in 1M sodium chloride (400 ml), methanol (533 ml) was added thereto, and the resultant precipitate was collected by centrifugation. The precipitate was dissolved in water (100 ml), and the solution was poured into ethanol (400 ml). The resultant precipitate was collected, washed-with ethanol and dried in vacuo to give 2.00 g of a low-molecular mannoglucan (MG10). Further, methanol (267 ml) was added to the supernatant obtained by the centrifugation just described above, and the resultant precipitate was collected. The precipitate was dissolved in water (60 ml) and poured into ethanol (240 ml). The resultant precipitate was collected, washed with ethanol and dried in vacuo to give 1.26 g of a low-molecular weight mannoglucan (MG4). The molecular weights of MG10 and MG4 (gel filtration method/standard substance: dextran, column: G4000PW$_{XL}$) were about 1×10$^5$ and about 4×10$^4$, respectively.

Example 11

MG15 (1.50 g) prepared in Example 9 was carboxymethylated in the same manner as Example 4 to give 1.80 g of MG15-CM-4 (degree of substitution: 0.52). 1.40 g of the MG15-CM-4 was carboxymethylated again in the same method as Example 5 to give 1.54 g of MG15-CM-5. The MG15-CM-5 (1.00 g) was further carboxymethylated in the same manner as Example 6 to give 1.08 g of MG15-CM-6 (degree of substitution: 1.0).

Example 12

MG10 (1.80 g) prepared in Example 10 was carboxymethylated in the same manner as Example 4 to give 2.23 g of MG10-CM-4. 2.00 g of the MG10-CM-4 was carboxymethylated again in the same method as Example 5 to give 2.25 g of MG10-CM-5. The MG10-CM-5 (1.0 g) was further carboxymethylated in the same manner as Example 6 to give 1.07 g of MG10-CM-6 (degree of substitution: 1.0).

Example 13

MG4 (500 mg) prepared in Example 10 was carboxymethylated in the same manner as Example 4 to give 594 mg of MG4-CM-4 (degree of substitution: 0.54).

Example 14

Mannoglucan (1.50 g) was dissolved in water (150 ml), a 8.5% aqueous sodium periodate solution (70 ml) was added thereto, and a reaction was allowed to proceed at room temperature for 64 hr. Ethylene glycol (1.7 g) was added to the reaction mixture, and the mixture was allowed to stand at room temperature for 2 hr and dialyzed against water. Sodium borohydride (0.75 g) was added to the inner solution, and a reaction was allowed to proceed at room temperature overnight. The pH of the reaction mixture was adjusted to 5 with acetic acid and then to 7 with 2 N sodium hydroxide. Thereafter, the mixture was dialyzed against water. The inner solution was concentrated to about 10 ml and poured into an ethanol (40 ml)/acetone (80 ml) mixed solvent, and the resultant precipitate was collected, washed with acetone and dried in vacuo to give 1.29 g of a mannoglucan polyalcohol (MG-PA).

Water (1 ml) and sodium hydroxide (2.0 g) were added to MG-PA (500 mg) with cooling to give a clear solution. Monochloroacetic acid (2.9 g) was added and dissolved in the solution, and a reaction was allowed to proceed at room temperature for 18 hr. After the pH of the reaction mixture was adjusted to 8 with acetic acid, the mixture was poured into ethanol (200 ml). Then the resultant precipitate was collected. The precipitate was washed with water (5 ml) and poured into methanol (125 ml). After that the resultant precipitate was washed with methanol and dried in vacuo to give 459 mg of a carboxymethylation product. 400 mg of the product was suspended in 2-propanol (40 ml), and the whole amount of a solution of 0.8 g of sodium hydroxide dissolved in 1.6 ml of water was dropwise added thereto. Thereafter, monochloroacetic acid (0.8 g) was added, and a reaction was allowed to proceed at room temperature for 20 hr with stirring. The precipitate in the reaction mixture was collected, dissolved in water (8 ml) and poured into methanol (200 ml). The resultant precipitate was collected, washed with methanol and dried in vacuo to give 631 mg of a carboxymethylated mannoglucan polyalcohol (MG-PA-CM). The degree of substitution (DS) of MG-PA-CM was measured in the same manner as Example 1 and found to be 9 per 4 saccharides. In this case, the DS value per 4 saccharides was determined by the following equation.

$$DS=16.2 \ (A-B)/([S-5.8 \ (A-B)]$$

Example 15

Figure 5:
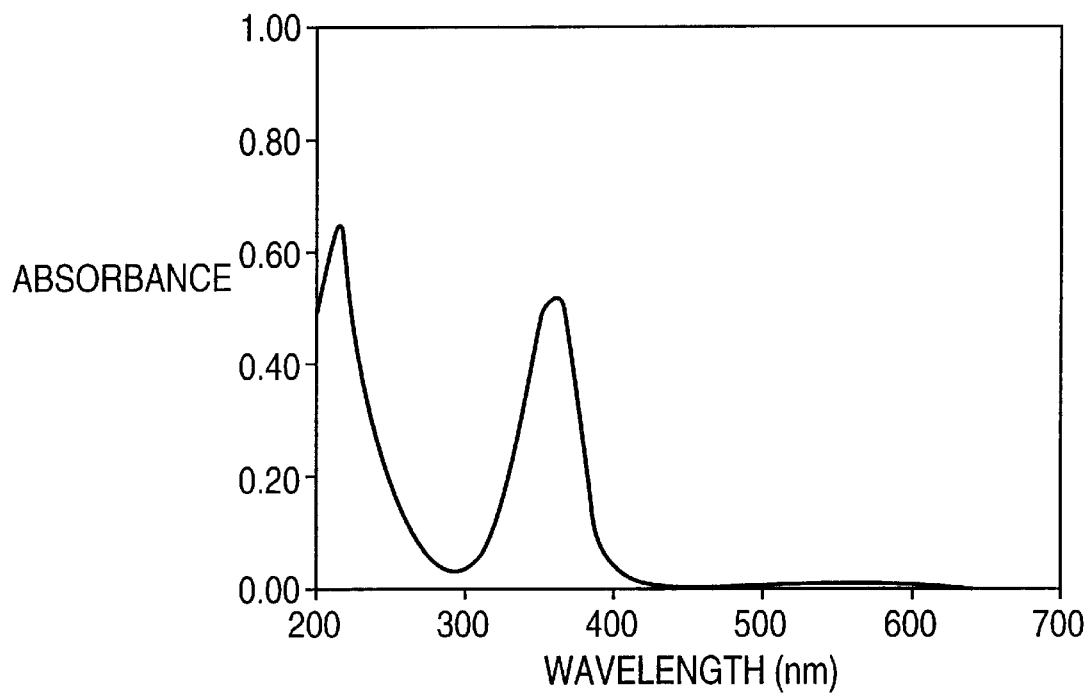
FIG. 5 is an ultraviolet-visible absorption spectrum of a carboxymethylmannoglucan-mitomycin C conjugate through an amide group prepared in Example 15.

50 mg of CM-5 prepared in Example 7 and 50 mg of 1-ethyl-3-(3-dimethylaminopropyl)carbodiimide hydrochloride (EDC) were dissolved in water (10 ml), and the solution was cooled with ice. A solution of 4 mg of mitomycin C (MMC) dissolved in 0.8 ml of water-ethanol (1:1, v/v) was prepared, and the whole amount of the solution was added to the above ice-cooled solution. A reaction was allowed to proceed for 1 hr with ice cooling while maintaining the pH of the reaction mixture at 5 to 6 with 0.2 N hydrochloric acid. After the pH of the reaction mixture was adjusted to 7.6 with 0.2 N sodium hydroxide, the mixture was poured into ethanol (50 ml). Then the resultant precipitate was collected, washed with 95% ethanol and dried in vacuo to give a conjugate comprising MMC bonded to CM-5 (52 mg). The MMC content of the conjugate was 7.6% (% by weight) as determined with an absorption at 365 nm. An ultraviolet-visible absorption spectrum of the conjugate (concentration: 96 µg/ml, solvent: water-ethanol (7:3, v/v) is shown in FIG. 5.

Example 16

CM-6 (50 mg) prepared in Example 7 was reacted with 4 mg of MMC by using 50 mg of EDC in the same manner as Example 15 to give a conjugate (50 mg) having a MMC content of 7.3% (% by weight).

Example 17

CM-7 (50 mg) prepared in Example 8 was reacted with 10 mg of MMC by using 150 mg of EDC in the same manner as Example 15 to give a conjugate (57 mg) having a MMC content of 14% (% by weight).

Example 18

Figure 6:
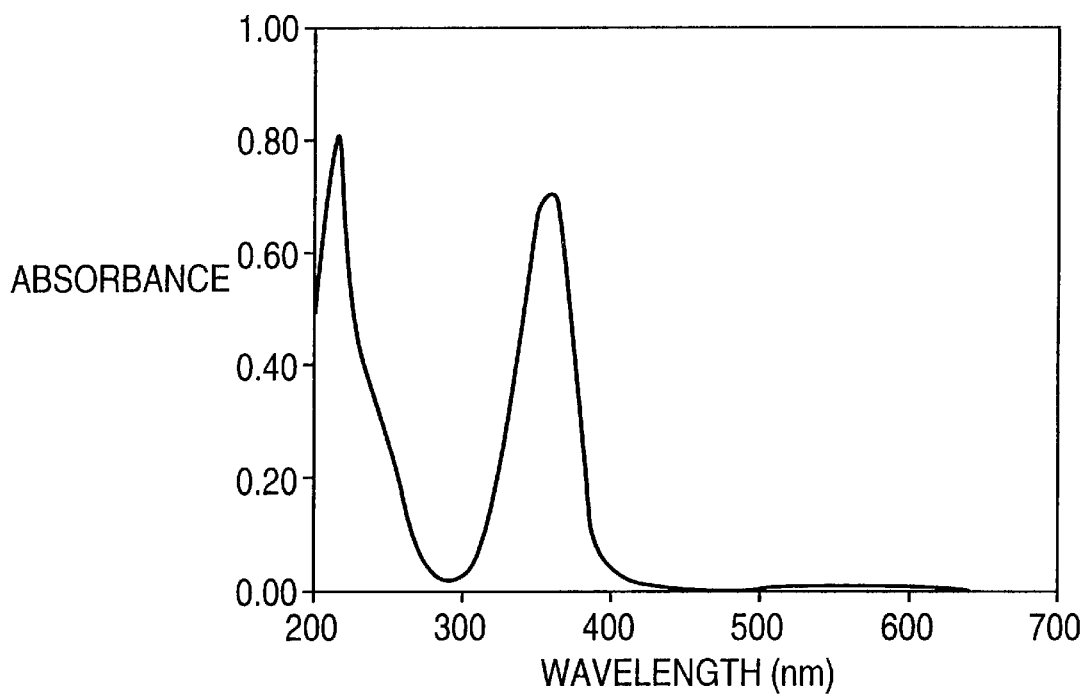
FIG. 6 is an ultraviolet-visible absorption spectrum of a carboxymethyl ring-opening-mannoglucan-mitomycin C conjugate through an amide group prepared in Example 18.
Figure 7:
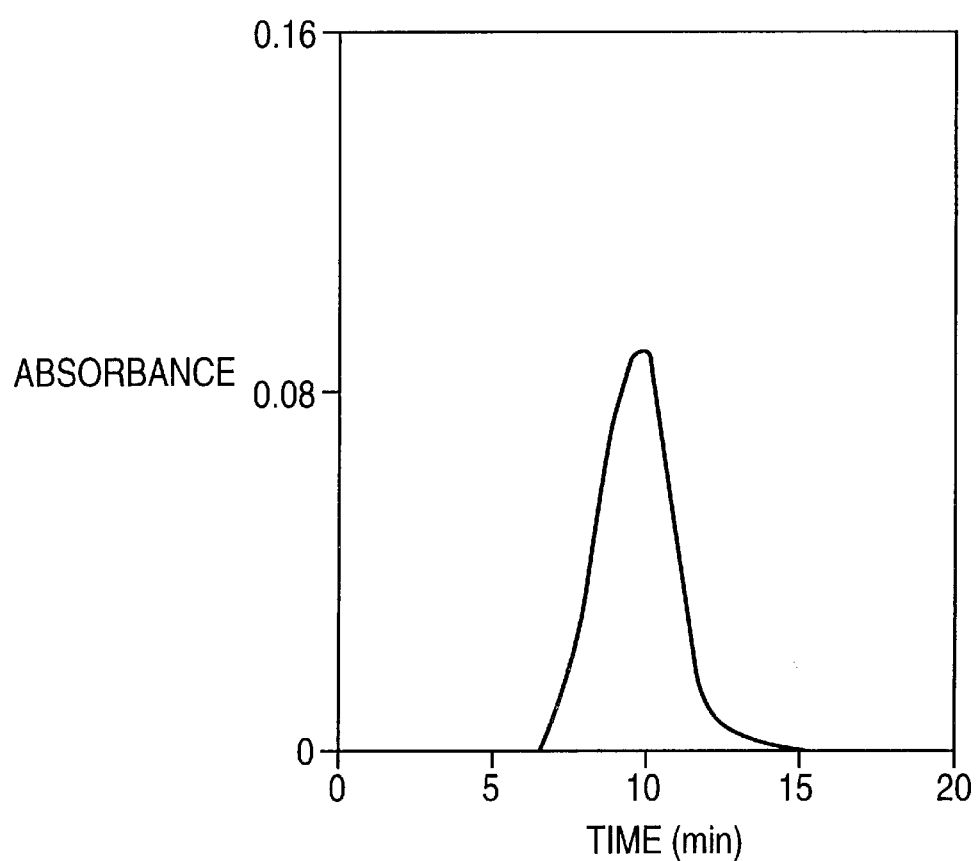
FIG. 7 is a gel filtration chromatogram of a carboxymethyl ring-opening-mannoglucan-mitomycin C conjugate through an amide group prepared in Example 18.

MG-PA-CM (30 mg) prepared in Example 14 was reacted with 10 mg of MMC by using 150 mg of EDC in the same manner as Example 15 to give a conjugate (31 mg) having a MMC content of 24% (% by weight). An ultraviolet-visible absorption spectrum (concentration: 42 μg/ml, solvent: water-ethanol (7:3, v/v) and a gel filtration chromatogram of the conjugate were as shown in FIGS. 6 and 7, respectively.

Example 19

MG15-CM-4 (50 mg) prepared in Example 11 was reacted with 4 mg of MMC by using 50 mg of EDC in the same manner as Example 15 to give a conjugate (53 mg) having a MMC content of 7.2% (% by weight).

Example 20

MG15-CM-6 (50 mg) prepared in Example 11 was reacted with 10 mg of MMC by using 150 mg of EDC in the same manner as Example 15 to give a conjugate (48 mg) having a MMC content of 15% (% by weight).

Example 21

MG10-CM-6 (50 mg) prepared in Example 12 was reacted with 10 mg of MMC by using 150 mg of EDC in the same manner as Example 15 to give a conjugate (55 mg) having a MC content of 17% (% by weight).

Example 22

MG4-CM-4 (50 mg) prepared in Example 13 was reacted with 4 mg of MMC by using 50 mg of EDC in the same manner as Example 15 to give a conjugate (46 mg) having a MMC content of 7.4% (% by weight).

Example 23

Figure 8:
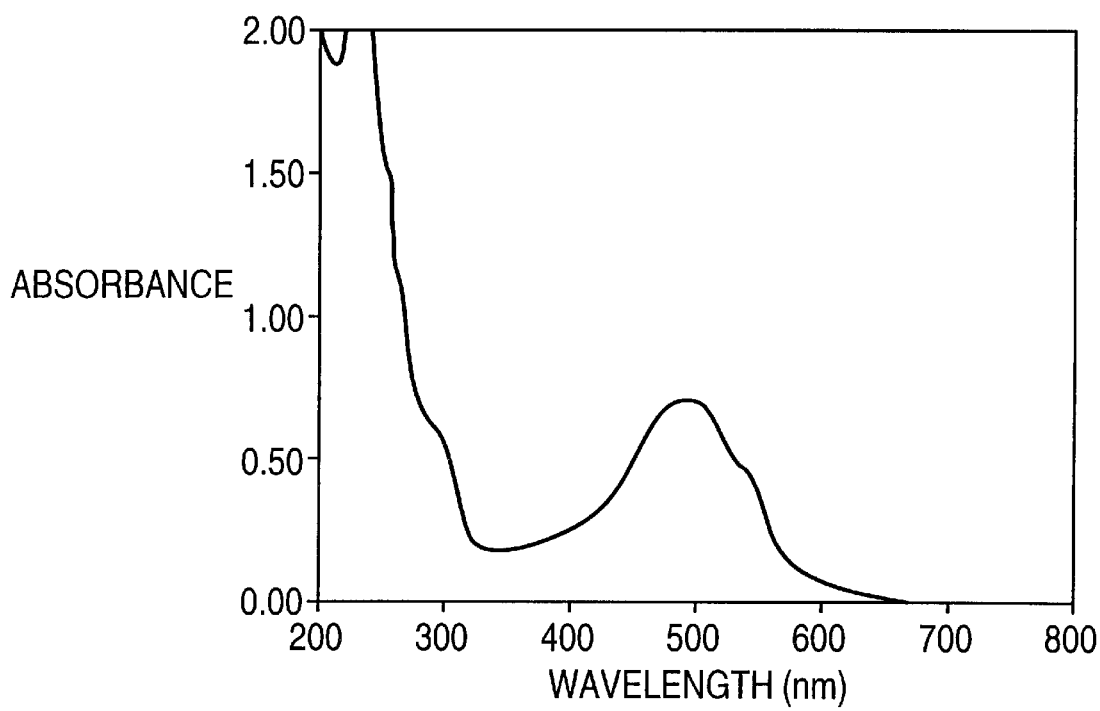
FIG. 8 is an ultraviolet-visible absorption spectrum of an oxidized carboxymethylmannoglucan-daunorubicin conjugate through a Schiff's base-type bond prepared in Example 23.

CM-4 (degree of substitution: 0.53, 1.25 g) prepared in the same manner as Example 4 was dissolved in water (300 ml). This solution was mixed with a solution of 3.32 g sodium periodate (3 molar equivalents per mole of saccharide residue) dissolved in water (200 ml). After the reaction was allowed to proceed at room temperature for one day, 1 g of ethylene glycol was added to the reaction mixture. Then the further reaction was allowed to proceed for 4 hr. The reaction mixture was dialyzed against water. And then the inner solution was concentrated. An ethanol-acetone mixed solution (about 1:1) was added to the concentrate, and methanol saturated with sodium acetate (15 ml) was dropwise added thereto. The resultant precipitate was collected to give 1.11 g of a carboxymethylmannoglucan having aldehyde groups. 800 mg of this product was dissolved in a 0.1M borate buffer (pH=8.0, 250 ml), and the solution was mixed with 160 ml of an ethanol solution containing 130 mg of daunorubicin hydrochloride. The mixture was stirred at room temperature for 16 hr. After a 3M sodium chloride solution (8 ml) was added to the mixture, the mixture was filtered. The filtrate was mixed with ethanol, and the resultant precipitate was collected to give 677 mg of a carboxymethylmannoglucan-daunorubicin composite. This conjugate was soluble in water and had a daunorubicin content of 10% (% by weight). An ultraviolet-visible absorption spectrum (concentration: 330 μg/ml, solvent: water) was as shown in FIG. 8.

Example 24

Figure 9:
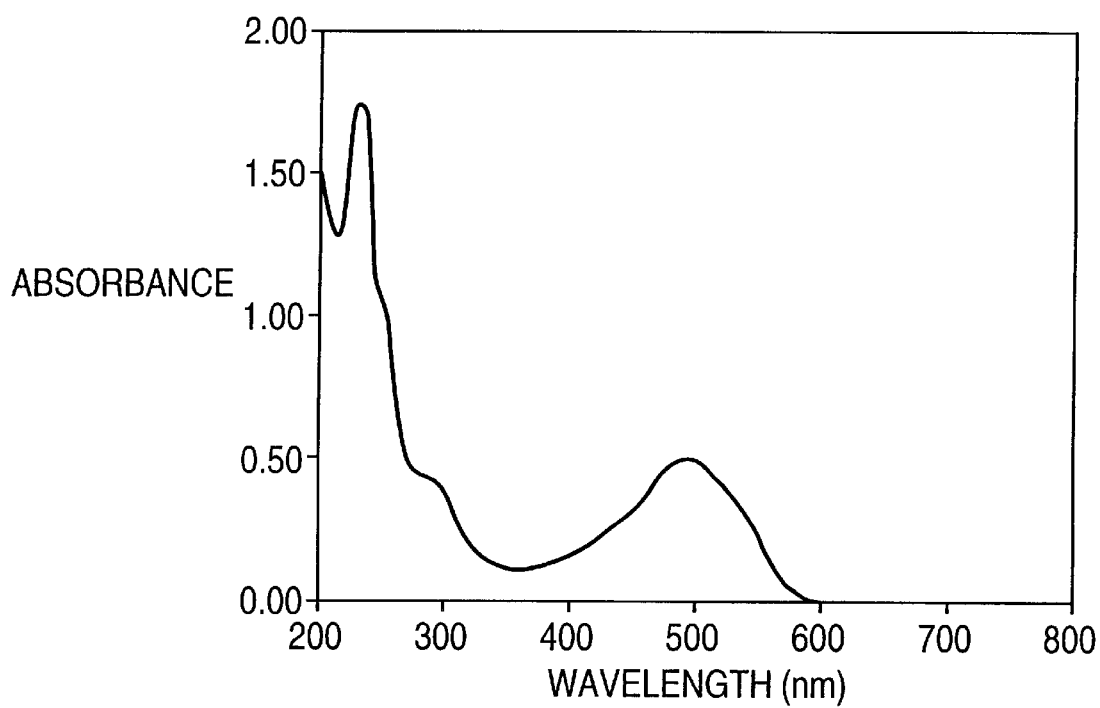
FIG. 9 is an ultraviolet-visible absorption spectrum of an oxidized carboxymethylmannoglucan-daunorubicin conjugate through a Schiff's base-type bond prepared in Example 24.

CM-6 (800 mg) prepared in Example 7 was dissolved in water (200 ml). The solution was mixed with a solution of 2.12 g (3 molar equivalents per mole of saccharide residue) of sodium periodate dissolved in water (30 ml). After the reaction was allowed to proceed at room temperature for one day, 620 mg of ethylene glycol was added to the mixture. And then a further reaction was allowed to proceed for 4 hr. The reaction mixture was dialyzed against water, and the resulting inner solution was concentrated. An ethanol-acetone mixed solution (about 1:1) was added thereto, methanol saturated with sodium acetate (10 ml) was dropwise added with stirring, and the resultant precipitate was collected to give 643 mg of a carboxymethylmannoglucan subjected to conversion to an aldehyde. 600 mg of the product was dissolved in a 0.1M borate buffer (pH=8.0, 175 ml), the solution was mixed with 110 ml of an ethanol solution containing 150 mg of daunorubicin hydrochloride, and the mixture was stirred at room temperature for 16 hr. A 3M sodium chloride solution (4.5 ml) was added thereto, and the mixture was filtered. The filtrate was mixed with ethanol, and the resultant precipitate was collected to give 610 mg of a carboxymethylmannoglucan-daunorubicin conjugate. The conjugate was soluble in water and had a daunorubicin content of 13% (% by weight). An ultraviolet-visible spectrum (concentration: 200 μ/ml, solvent: water) of the conjugate is shown in FIG. 9.

Example 25

Figure 10:
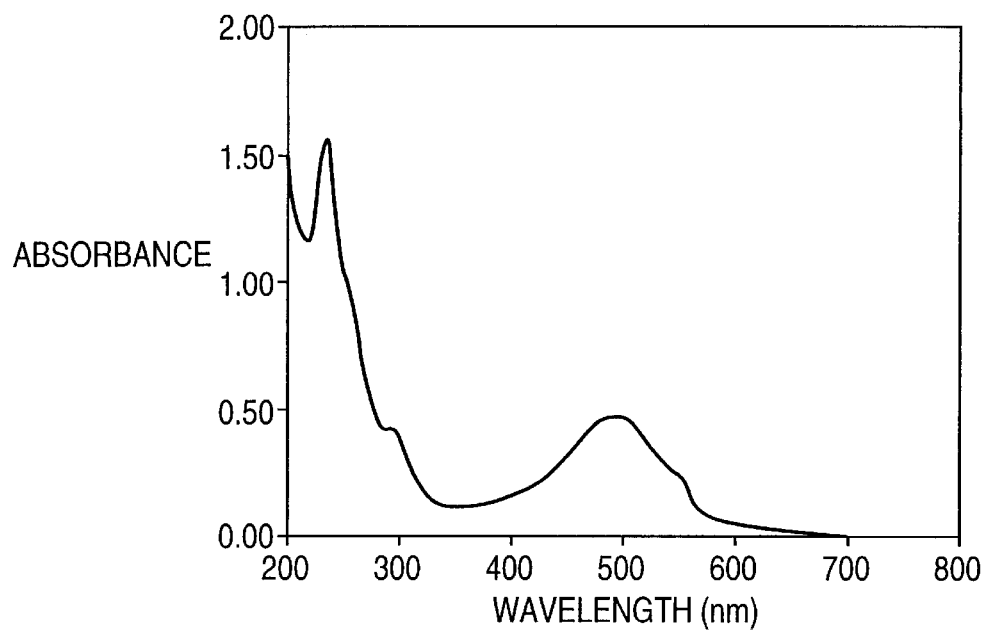
FIG. 10 is an ultraviolet-visible absorption spectrum of an oxidized carboxymethylmannoglucandaunorubicin conjugate through a Schiff's base-type bond prepared in Example 25.

MG10-CM-6 (700 mg) prepared in Example 12 was dissolved in water (175 ml). The solution was mixed with a solution of 1.86 g (3 molar equivalents per mole of saccharide residue) of sodium periodate dissolved in water (25 ml). After the reaction was allowed to proceed at room temperature for one day, 560 mg of ethylene glycol was added to the mixture. And then a further reaction was allowed to proceed for 4 hr. The reaction mixture was dialyzed against water, and the resulting inner solution was concentrated. An ethanor-acetone mixed solution (about 1:1) was added thereto, methanol saturated with sodium acetate (8 ml) was added thereto, and the resultant precipitate was collected to give 571 g of a carboxymethylmannoglucan subjected to conversion to an aldehyde. 571 mg of the product was dissolved in a 0.1M borate buffer (pH=8.0, 180 ml), the solution was mixed with 112 ml of an ethanol solution containing 143 mg of daunorubicin hydrochloride, and the mixture was stirred at room temperature for 16 hr. A 3M sodium chloride solution (3 ml) was added thereto, and the mixture was filtered. The filtrate was mixed with ethanol, and the resultant precipitate was collected to give 610 mg of a carboxymethylmannoglucan-daunorubicin conjugate. The conjugate was soluble in water and had a daunorubicin content of 12% (% by weight). An ultraviolet-visible spectrum (concentration: 200 μg/ml, solvent: water) of the conjugate is shown in FIG. 10.

Example 26

Cis-dinitratediammine-platinum (II) as a platinum complex was synthesized by a known method (for example, Inorg. Chem., Vol. 16, p. 1525 (1977), B. Lippert et al.)

Figure 11:
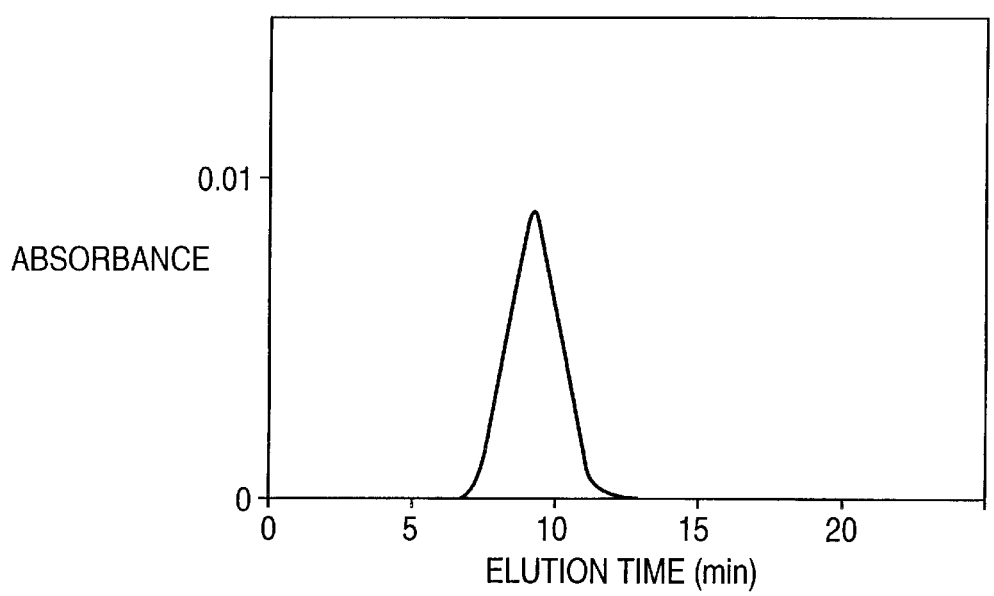
FIG. 11 is a gel filtration elution pattern of a cis-diammine-platinum (II) complex through a covalent bond prepared in Example 26.

MG-PA-CM (230 mg) prepared in Example 14 was dissolved in water (7 ml), a solution of cisdinitratediammine-platinum (II) (24.71 mg) dissolved in water (7 ml) was added thereto, and a reaction was allowed to proceed at room temperature for 24 hr under a light shielding condition. After it was confirmed by gel filtration chromatography that no platinum complex as a starting compound remained, the reaction mixture was dialyzed against water overnight. After the pH of the inner solution was adjusted to 6.5 with 1 N NaOH, the solution was concentrated to about 10 ml. Ethanol (80 ml) was added thereto, the resultant precipitate was collected and dried in vacuo to give a cis-diammine-platinum (II) complex (218 mg, platinum content (by atomic absorption method): 5.90%). A gel filtration elution pattern (detection: ultraviolet absorption at 280 nm) of the complex is shown in FIG. 11.

Example 27

A cis-diammine-platinum (II) complex (12.6 mg, platinum content: 7.04%) was prepared from CM-6 (14.6 mg) prepared in example 7 and cis-dinitratediammine-platinum (II) (2.12 mg) in the same manner as Example 26.

Example 28

A cis-diammine-platinum (II) complex (205 mg, platinum content: 6.60%) was prepared from CM-7 (211 mg) prepared in Example 8 and cis-dinitratediammine-platinum (II) (24.7 mg) in the same manner as Example 26.

We claim:

1. A carboxymethylmannoglucan derivative comprising tetrasaccharide units represented by the following general formula (III) or salt thereof:

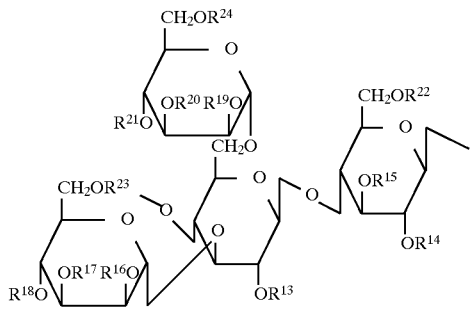
(III)

wherein $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ which may be the same or different each represent a hydrogen atom, $CH_2COOH$, $CH_2CONR^{*1}R^{*2}$ wherein $NR^{*1}R^{*2}$ represents a residue formed by removing one hydrogen atom from an amino group of a drug which has an amino group and is represented by the general formula $HNR^{*1}R^{*2}$, $CE_2COOR^{*3}$ wherein $OR^{*3}$ represents a residue formed by removing a hydrogen atom from an alcoholic hydroxyl group of a drug which has an alcoholic hydroxyl group and is represented by the general formula $HOR^{*3}$, or $[CH_2COO\cdot\frac{1}{2}[Pt(NH_3)_2]]$ wherein Pt represents a divalent platinum, with the proviso that at least one of $R^{13}$ to $R^{24}$ in the molecule represents $CH_2CONR^{*1}R^{*2}$, $CH_2COOR^{*3}$ or $[CH_2COO\cdot\frac{1}{2}[Pt(NH_3)_2]]$.

2. A carboxymethylmannoglucan derivative or salt thereof according to claim 1, which has a molecular weight of 10,000 to 2,000,000.

3. A carboxymethylmannoglucan derivative or salt thereof according to claim 1 or 2, which has a degree of substitution, defined as the number of carboxymethyl groups per saccaride residue of 0.01 to 3.0.

4. A process for preparing a carboxymethylmannoglucan derivative or salt thereof according to any one of claims 1 or 2, comprising reacting a compound or salt thereof of the formula

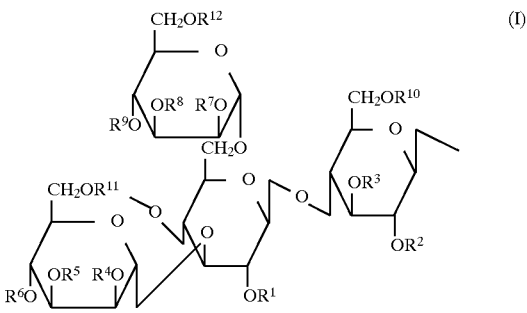
(I)

wherein $R^1$, $R^2$, $R^3$, $R^4$, $R^5$, $R^6$, $R^7$, $R^8$, $R^9$, $R^{10}$, $R^{11}$ and $R^{12}$ may be the same or different, each representing a hydrogen atom or $CH_2COOH$, with $HNR^{*1}R^{*2}$, $HOR^{*3}$ or $Pt(NH_3)_2(NO_3)_2$.

5. A process for preparing a carboxymethylmannoglucan derivative or salt thereof according to claim 3, comprising reacting a carboxymethylmannoglucan comprising tetrasaccharide units represented by the following general formula (I) or salt thereof,

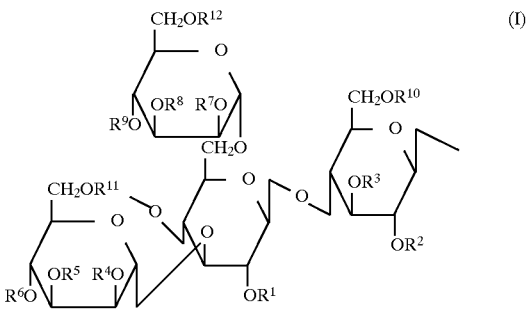
(I)

wherein $R^1$, $R^2$, $R^3$, $R^4$, $R^5$, $R^6$, $R^7$, $R^8$, $R^9$, $R^{10}$, $R^{11}$ and $R^{12}$, which may the same or different, each represent a hydrogen atom or $CH_2COOH$, with $HNR^{*1}R^{*2}$, $HOR^{*3}$ or $Pt(NH_3)_2(NO_3)_2$.

6. A method for transferring a drug to a tumor in a mammal, comprising the step of administering a carboxymethylmannoglucan derivative comprising tetrasaccharide units represented by the following general formula (III) or salt thereof:

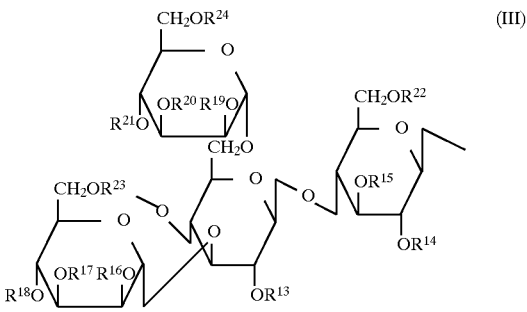
(III)

wherein $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$, which may be the same or different, each represent a hydrogen atom, $CH_2COOH$, $CH_2CONR^{*1}R^{*2}$, wherein $NR^{*1}R^{*2*}$ represents a residue formed by removing one hydrogen atom from an amino group of a drug which has an amino group and is represented by the general formula $HNR^{*1}R^{*2}$, $CH_2COOR^{*3}$, wherein $OR^{*3}$ represents a residue formed by removing a hydrogen atom from an alcoholic hydroxyl group of a drug which has an alcoholic hydroxyl group and is represented by the general formula $HOR^{*3}$, or, wherein Pt represents a divalent platinum, with the proviso that at least one of $R^{13}$ to $R^{24}$ in the molecule represents $CH_2CONR^{*1}R^{*2}$, $CH_2COOR^{*3}$ or, to said mammal.

* * * * *